US011008233B2

(12) United States Patent
Volker

(10) Patent No.: US 11,008,233 B2
(45) Date of Patent: May 18, 2021

(54) CHLORINE MEASUREMENT/FILTER TESTING/BRINE CONTAINER MONITORING OF A WATER TREATMENT SYSTEM

(71) Applicant: Vivonic GmbH, Sailauf (DE)

(72) Inventor: Manfred Volker, Blankenbach (DE)

(73) Assignee: Vivonic GmbH, Sailauf (DE)

( * ) Notice: Subject to any disclaimer, the term of this patent is extended or adjusted under 35 U.S.C. 154(b) by 51 days.

(21) Appl. No.: 16/558,733

(22) Filed: Sep. 3, 2019

(65) Prior Publication Data

US 2019/0389747 A1    Dec. 26, 2019

Related U.S. Application Data

(63) Continuation of application No. 14/315,530, filed on Jun. 26, 2014, now Pat. No. 10,550,017.

(30) Foreign Application Priority Data

Jul. 13, 2013    (DE) .................... 10 2013 011 752.6

(51) Int. Cl.

| C02F 1/00 | (2006.01) |
|---|---|
| C02F 1/467 | (2006.01) |
| C02F 1/461 | (2006.01) |
| G01N 33/18 | (2006.01) |
| C02F 1/42 | (2006.01) |
| C02F 5/08 | (2006.01) |

(52) U.S. Cl.
CPC .......... *C02F 1/4674* (2013.01); *C02F 1/008* (2013.01); *C02F 1/4618* (2013.01); *G01N 33/18* (2013.01); *C02F 1/42* (2013.01); *C02F 5/08* (2013.01); *C02F 2201/46125* (2013.01); *C02F 2209/29* (2013.01); *C02F 2303/04* (2013.01); *C02F 2303/16* (2013.01); *C02F 2303/185* (2013.01)

(58) Field of Classification Search
CPC .................................................. C02F 2209/29
USPC ........................................................ 73/1.02
See application file for complete search history.

(56) References Cited

U.S. PATENT DOCUMENTS

| 3,456,801 A | 7/1969 | Bowles |
| 5,041,196 A | 8/1991 | Cawlfield et al. |
| 5,326,481 A | 7/1994 | Alwerud |
| 7,883,622 B1 | 2/2011 | Barnes |
| 7,985,377 B2 * | 7/2011 | Vincent .............. G01N 27/4168 |
| | | 422/82.01 |
| 9,188,476 B2 | 11/2015 | Volker |
| 9,422,175 B2 | 8/2016 | Volker |

(Continued)

FOREIGN PATENT DOCUMENTS

IT    1244040 B    7/1994

OTHER PUBLICATIONS

ChemIndustrial Systems, Inc., Advantages of ChemIndustrial pumped venturi metering pumps vs piston and diaphragm pumps, Chem. Industrial, Aug. 26, 2010, pp. 1-3.

*Primary Examiner* — Chester T Barry
(74) *Attorney, Agent, or Firm* — Greer, Burns & Crain, Ltd.

(57) ABSTRACT

A water treatment system, particularly pre-filtration unit of the water treatment system, comprising at least one chlorine sensor device, includes a salt-water treatment device which is connected to the chlorine sensor device, an electrolysis cell being disposed in the associated line, and thereafter a pump and a release valve.

18 Claims, 3 Drawing Sheets

(56) References Cited

U.S. PATENT DOCUMENTS

| | | | |
|---|---|---|---|
| 9,862,618 B2 | 1/2018 | Volker | |
| 2001/0004962 A1* | 6/2001 | Hirota | C02F 1/46104 |
| | | | 204/228.1 |
| 2002/0195403 A1* | 12/2002 | Takeda | C02F 1/42 |
| | | | 210/749 |
| 2003/0029808 A1 | 2/2003 | Yamamoto et al. | |
| 2004/0211731 A1 | 10/2004 | Ferguson et al. | |
| 2005/0082164 A1 | 4/2005 | Inamoto et al. | |
| 2005/0173262 A1* | 8/2005 | Nakanishi | C02F 1/46104 |
| | | | 205/743 |
| 2006/0027463 A1 | 2/2006 | Lavelle et al. | |
| 2008/0046215 A1 | 2/2008 | Nelson et al. | |
| 2009/0057145 A1* | 3/2009 | Vincent | G01N 27/4168 |
| | | | 204/401 |
| 2010/0206788 A1 | 8/2010 | Von Broembsen et al. | |
| 2011/0024361 A1 | 2/2011 | Schwartzel et al. | |
| 2011/0094949 A1* | 4/2011 | Just | C02F 1/688 |
| | | | 210/85 |
| 2012/0000488 A1* | 1/2012 | Herdt | C11D 3/0047 |
| | | | 134/18 |
| 2016/0030653 A1* | 2/2016 | White | C02F 1/50 |
| | | | 210/646 |
| 2020/0375189 A1* | 12/2020 | Alimi | A61L 2/0088 |

* cited by examiner

CHLORINE MEASUREMENT/FILTER TESTING/BRINE CONTAINER MONITORING OF A WATER TREATMENT SYSTEM

RELATED APPLICATIONS

This application is a continuation of U.S. application Ser. No. 14/315,530 filed on Jun. 26, 2014, which claims priority to German Patent Application No. 10 2013 011 752.6 filed on Jul. 13, 2013, the entireties of which are both incorporated herein by reference.

FIELD OF THE INVENTION

The present invention refers to a fluid system for quality/function monitoring and/or control of physically and chemically acting filter stages of a water pretreatment for the operation of a reverse-osmosis or another water treatment or water monitoring system.

BACKGROUND OF THE INVENTION

Filter routes have the disadvantage that the remote diagnosis of chlorine and hardness and the monitoring of the degree of soiling of mechanical filters cannot be carried out or can only be carried out by taking great efforts.

Moreover, it is necessary for reasons of safety, particularly in dialysis water treatments, that a time-consuming manual documentation of the water hardness and/or of the chlorine content should be carried out daily, especially in order to furnish evidence that the toxic chlorine has been removed from the liquid by the filters used.

Existing chlorine sensors for online measurement are often not chlorinated at regular intervals and cannot provide any reliable measurement results in the absence of chlorine in the liquid.

To remove hardly soluble salts, such as calcium and/or magnesium, from the water, softeners are often used. When softeners are used with acidic cation exchange resins, these must be regenerated by means of sodium chloride brine solution at regular intervals.

This regeneration is normally carried out with sodium chloride solution which is provided in a so-called brine container in which salt is dissolved in a predetermined liquid amount.

Failure of the regeneration process e.g. because of a missing sodium chlorine brine solution may lead to serious calcification of the downstream systems.

Moreover, softeners tend to show a microbial growth with subsequent contamination of the liquid flowing therethrough because of the relatively large resin volume.

Problems are posed by filter blocking because the resulting exchange of filter material is normally accompanied by operational interruption.

BRIEF SUMMARY OF THE INVENTION

The aim of the invention is the development of an actuator-sensor control which enables the user to evaluate the functionality of a system by online access and to obtain, on this basis, a remote diagnosis about the current operational state.

To meet the normative and/or in-house requirements, the necessary documentation evidence can be furnished simultaneously together with the automatic recording by way of the connected electronic data processing system.

It is possible on account of the desired system-specific evaluation by analysis and visualization of the operational parameters to achieve an acyclic distribution of the service operations and thus a reduction of the number of services.

On this basis an economic and ecological procedure is possible as the deployment of trained stuff on site can thereby be coordinated in an improved way and failure caused by wear can be avoided in a targeted and preventive way.

To avoid the aforementioned drawbacks and to comply with the objective, respectively, partial streams are passed under one aspect of the present invention to the corresponding sensor before and after the filter stages by means of switched valves and are evaluated by electronic measuring devices. These measuring devices may here also be an integral part of subsequent systems of a water treatment and/or also a control room, and a bidirectional operation for influencing actuators and sensors is here possible.

Advantageously, with an electronic pressure sensor different mechanical filter stages are monitored online with respect to their degree of soiling by measuring the pressures and determining the pressure difference and an automatic backwashing program is also started in the case of suitable filters with a corresponding automatic backwashing system.

Under another aspect of the invention, use is made of an online measuring chlorine sensor the safety-relevant function of which is checked according to the invention by supplying electrolytically produced chlorine of a known concentration to the sensor at regular intervals.

The measurement result is electronically recorded and documented. The chlorine can be produced from an existing brine solution.

The function of the softener, i.e. the filtration and reduction of the hardly soluble calcium and magnesium salts, can be monitored by an ion-sensitive calcium and/or magnesium sensor.

The fill level of the salt water container and the residual volume of the salts in the brine container, respectively, have to be monitored in a simple way by means of a weighing device. To this end the brine container is placed on a constructional element with weighing cell. Since the constructional understructure can be used at any time independently of the brine container used, brine containers that are already in use can also be equipped with the monitoring device.

It is possible to indicate the brine volume directly or as a signal-light solution with message color; transfer to and recording in a control room or a subsequent water treatment system, which may e.g. be configured as an RO system, is also possible. Inspection and documentation of the salt supply in the brine container which has to be carried out by the operating personnel every day can thus be dispensed with.

A regular slight chlorination of the softener during regeneration by chlorine, which is electrolytically produced from the brine container of the softener, reduces the microbial growth in the softener resin and thereby ensures a more sterile liquid.

DETAILED DESCRIPTION OF THE INVENTION

Figure 1:
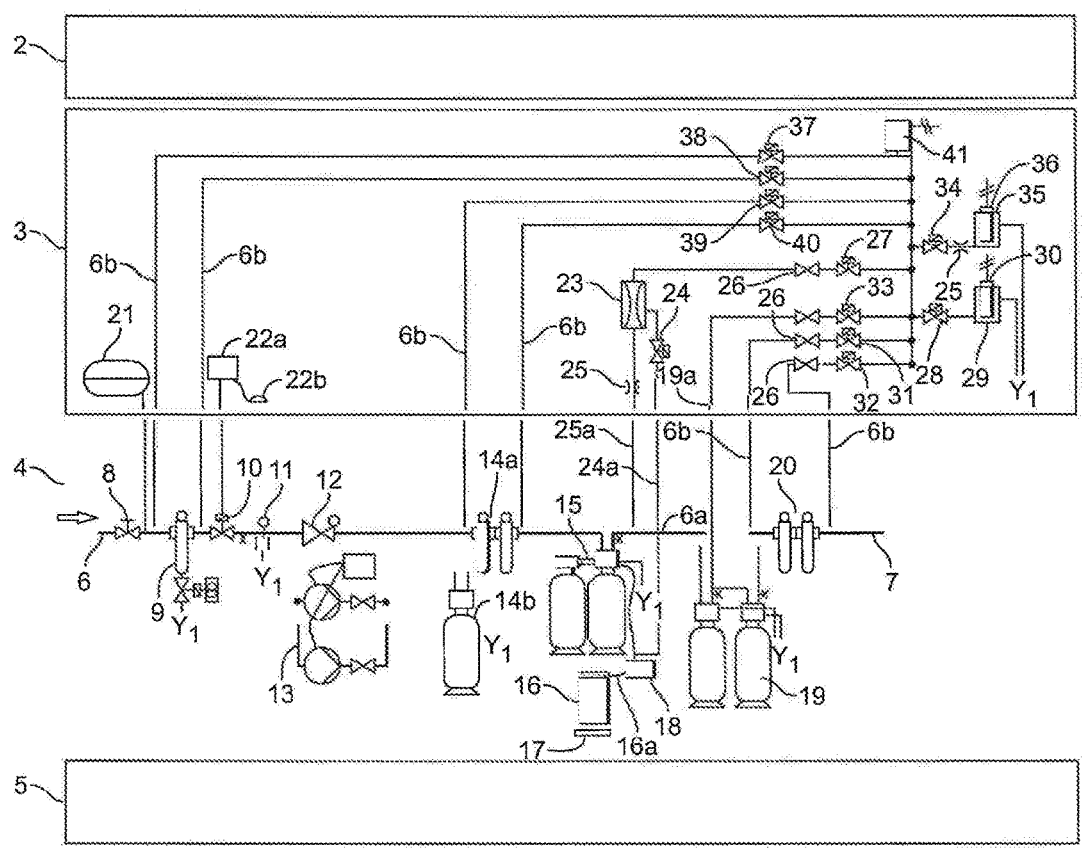
FIG. 1 is a schematic diagram of a pre-filtration unit according to the invention.
Figure 2A:
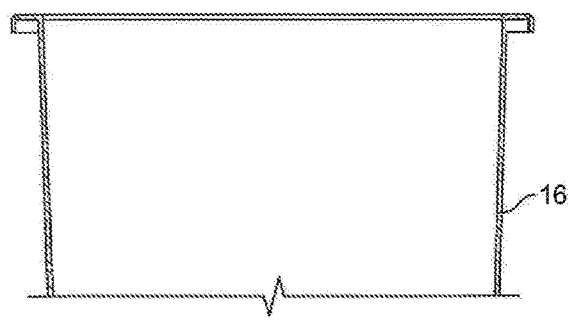
FIG. 2a is a cross-sectional view of a salt water container according to the invention.
Figure 2A:
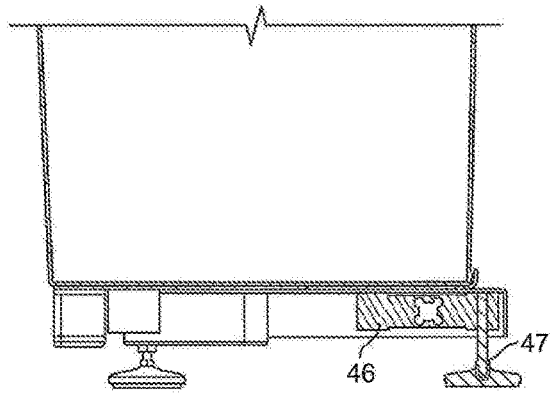
Figure 2B:
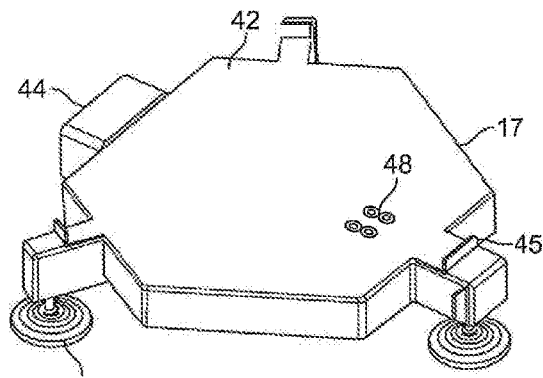
FIG. 2b is a top perspective view of a weighing platform according to the invention.
Figure 2C:
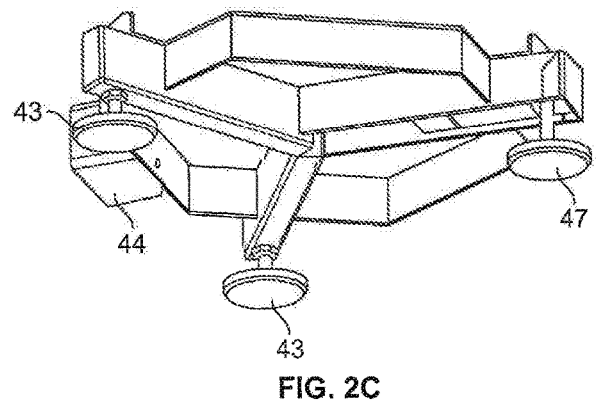
FIG. 2c is a bottom perspective view of the weighing platform of FIG. 2b.

FIG. 1 shows a pre-filtration unit according to the invention with a mechanical-chemical filter stage 4, an actuator-sensor monitoring unit 3, an associated electronic evaluation unit 2, and a possible electronic unit 5 pertaining e.g. to a downstream reverse osmosis system, wherein the electronic unit 2 may also be configured as a control-room electronic unit and may communicate with the electronic unit 5.

The mechanical-chemical filter stage 4 is only shown by way of example with respect to the selection of the arranged filter stages so to as to illustrate the function of the monitoring operation according to the invention.

The exemplary arrangement of a water line 6a begins with the water inlet 6, a shut-off valve 8, and an automatically back-washable pre-filter 9 with drain valve and drainage connection. This is followed by a safety shut-off valve 10 which is activated by a leakage indicator 22a with liquid sensor 22b.

Further components may be a pipe separator 11 and a backflow preventer 12 for avoiding contamination of the water inlet 6.

At low water supply pressures it is possible to add a pressure increasing unit 13. A further possible filter stage 14 may be configured as a cartridge filter 14a, sand filter (14b) or also as a hollow fiber filter (here not shown) in the nano or ultra-pore range.

A softener 15, e.g. illustrated as a twin softener, is normally filled with strongly acidic, cation-containing resin which upon exhaustion has to be regularly regenerated with NaCl solution from the salt water treatment 16. It is here important to monitor the fill level of the salt in the salt water container 16. This is done with a weighing device 17, which is designed as an independent constructional understructure.

According to FIG. 2 the weighing device 17 consists of a weighing cell 46 the signal of which can be amplified by electronics 44 on the weighing platform 42, electronically processed, or can be processed by electronics 2 and also by possibly successive electronics 5. Preset weight limit values of the brine container can here be monitored and optically or acoustically indicated or remotely diagnosed by technical electronic data processing. The weighing cell 46 is fastened to the weighing platform 42 by means of screws 48 such that a third of the brine or salt weight weighs on the measuring foot 47. Side boundaries 45 are mounted for the lateral guidance of the brine container.

During the regeneration process of the softener 15 chlorine-containing solution can be formed with the help of an electrolysis device 18 from the salt water flowing towards the electrolysis cell 18. It goes without saying that the chlorine concentration depends on the brine concentration, but substantially on the magnitude of the electrically supplied power to the electrolysis cell. The microbial growth in the softener resin is thereby strongly reduced.

19 shows a twin carbon filter/dechlorination device which is used for the filtration of the chlorine.

A filter stage 20 as a fine-filter stage can remove the smallest particles from the filter water 7 before it is e.g. supplied to a reverse osmosis system or a drinking water installation.

The actuator-sensor unit 3 can be equipped with an electronic water meter 21 for recording and reporting the water consumption.

For monitoring the chlorine content of the supplied liquid a chlorine sensor 30 is preferably positioned in a chlorine sensor chamber 29, either for the measurement of the whole chlorine or of the free chlorine. The chlorine sensor chamber 29 has an inlet and a free outlet. A release valve 28 is directly positioned in front of the sensor chamber. Usually, the supplied liquid can be chlorinated by the water supplier with chlorine of different concentrations; depending on the hygienic state, a chlorine input may be temporarily missing. In such a case no statement can be made on the proper function of the sensor 30 without further measure.

For regularly checking the chlorine sensor a test valve 27, a brine suction valve 24, and the release valve 28 are opened and the electrolysis cell 18 is switched on. The brine or the chlorine-containing solution is sucked in a selected concentration ratio from the brine container 16 via the adjustable brine suction valve 24 and a pump 23, mixed with liquid via a flow throttle 25, passed on to the measuring chamber 29, recorded via the chlorine sensor 30 and evaluated with electronics 2 and 5, respectively.

The proper function of the measuring cell 30 can be ensured by this regular testing. It is within the scope of the present invention to provide and monitor the sodium chloride brine solution also exclusively for the purpose of chlorine sensor monitoring, independently of a softener or other filter stages. The suction line of the brine solution and the electrolysis cell for the electrolytic chlorine production are here made independent of a brine suction line and an electrolysis cell of the softener.

Pump 23 is preferably shown as a venturi pump, but other pump types are possible for performing the function; in such a case the chlorine-containing solution is supplied in metered amounts by means of a pump (not shown) from line 24a into line 25a.

For monitoring the correct carbon filter function/dechlorination device 19 an upstream valve, e.g. 40 or 27, may first be opened. Likewise, the release valve 28 is opened. If chlorine is contained in the supplied liquid, this is recorded via the previously verified chlorine sensor 30.

Thereupon, the valves 33 after the first filter stage, 31 after the second filter stage or also 32 after a filter stage 20 and the chlorine release valve 28 are successively opened. The filter stages of the carbon filter can thus be tested. If the chlorine sensor records the absence of chlorine, the checking of the filter is successfully completed. It is within the meaning of the present invention that this measurement can also be carried out independently and recorded technically by electronic data processing.

Figure 3:
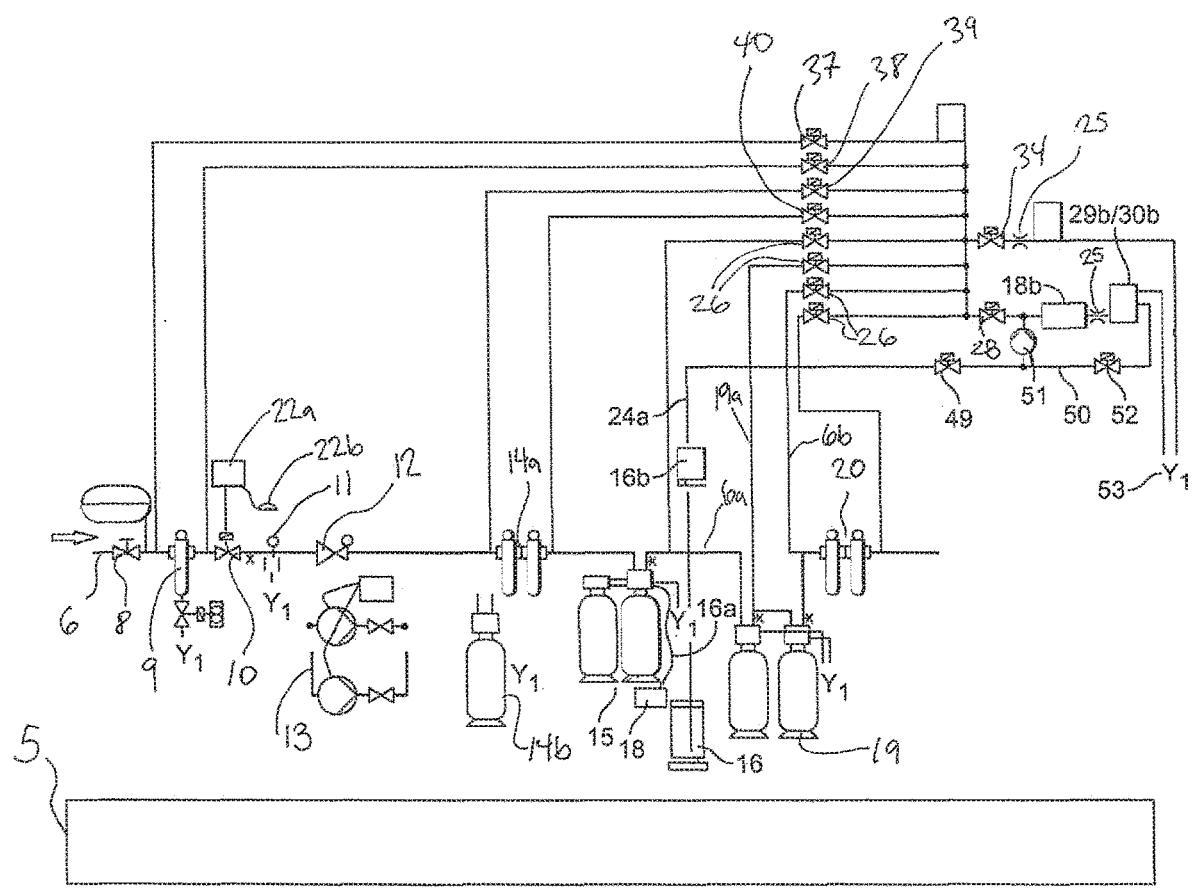
FIG. 3 is a schematic of an alternate embodiment of a pre-filtration unit according to the invention.

FIG. 3 shows a further pre-filtration unit of the invention which differs from that of FIG. 1 by the measures for ensuring a proper function of the chlorine measurement cell and for checking the same. Brine or chlorine-containing solution is sucked in a predetermined concentration ratio either from the brine container 16, which is arranged for the regeneration of the softener 15, or from a separately provided brine container 16b. The associated chlorine test line 24a terminates behind a shut-off valve 49 in a chlorine-test circulation circuit 50 in which in clockwise direction in which the sucked brine is circulated a pump 51, an electrolysis cell 18b and a measurement chamber 29b with a chlorine sensor and a further shut-off valve 52 are installed one after the other. The chlorine measurement chamber 29b is connected to a free outlet 53 as is also the case in the embodiment of FIG. 1. In this embodiment the brine is sucked—in contrast to the embodiment of FIG. 1—directly from the brine container 16 and is not branched off as a chlorine-containing liquid from the connection line 16a between the electrolysis cell 18 and the softener 15.

A small brine amount is here taken from the brine container 16 provided for the regeneration of the softener 15 or from an optionally available brine container 16b and circulated through the chlorine generator 18b and the chlorine measurement cell 29b. This is preferably done at regular time intervals to keep the chlorine measurement cell active and to perform a function control. The chlorine measurement cell or the chlorine sensor 30, respectively, is here to indicate a measurement value within a predetermined range with a short, always identical switch-on period of the chlorine generator 18b. After this activation and detection the whole line towards the brine container is flushed free. The flushing interval is defined such that the brine amount taken is replenished.

It is within the scope of the invention that, instead of the brine container 16b, a container with chlorine bleaching agent or chlorine dioxide or a similar chlorine-containing liquid is used. In this case the chlorine generator 18b is omitted.

With the above-described activation of the chlorine measurement cell it is reliably prevented that this cell becomes passive. Only minimum amounts of NaCl are here consumed.

Apart from the above-described features for activation and control of the chlorine measurement cell, the pre-filtration unit of FIG. 3 corresponds to that of FIG. 1, so that the reference numerals thereof are also applicable to the embodiment of FIG. 3. The arrangement of the eight valves 37, 38, 39, 40, 27, 33, 31, 32 is shown in a purely schematic manner. These valves and their associated actuating members, which are also called actuators in the description, may be provided—other than shown in the drawings—also at the places where the associated branch lines branch off from the water line 6a.

For monitoring the filter stages 9, 14, 20 a pressure sensor 41 is acted upon selectively and successively before or after the filter stages with the pressures prevailing at the filter stages via the valves 37, 38, 39, 40, 31, 32 shown in FIG. 1.

For instance, the pressure drop of the filter stage 9 is monitored by measuring the inlet pressure via the upstream valve 37 and the outlet pressure is monitored by the subsequent valve 38.

As an equivalent to the said measurement, FIG. 1 shows the measurement of the pressure drops by switching the valves 39/40 for the filter stage 14 and the valves 31/32 for filter stage 20.

The determination of the pressure drops at the softening stage 15 and dechlorination stage 19 is also possible by way of a successive switching of the valves 40, 27, 33, 31.

An atmospheric relief of the pressure sensor 41 in general or between two measurements can be carried out via valve 34 and also 28.

By measurement of the flow through line 6a with water meter/flow meter 21 or also by a corresponding flow measurement in a subsequent treatment process, the pressure values measured on the filters can be calculated by means of electronics 2, 5 as standard or mean values and a warning, exchange, flushing or maintenance time can be predicted for preset pressure differences.

Since the determination of the filter pressure differences normally regards relative measurements, the use of a single pressure sensor 41 is advantageous both in terms of costs and in terms of the calibration efforts.

As a rule, the water inlet pressures on line 6a, e.g. on filter 9, are known, so that the pressure sensor 41, acted upon with a known pressure before the beginning of a measurement cycle, must be verified during maintenance or during inspection by a technician.

An advantageous development of the pressure measurement is the determination of mean pressure values by means of electronics 2, 5 on the respective filters 9, 14, 15, 19, 20 in that e.g. 50 measurements are combined to form a mean value and are represented over an exemplary period of 1000 operating hours. Changes that are due to the service life end of the sensor 41 or the blocking of the aforementioned filters can be recognized technically by electronic data processing or predicted, respectively, and remotely inquired.

To monitor the correct function of the softener 15, valve 40 is first of all opened and hard water is supplied via a measuring chamber 35 to a calcium sensor 36 through the opened valve 34.

Subsequently, softened liquid is passed via the flow throttle 25 and valves 27, 34 into the measuring chamber 35 to the ion-sensitive calcium sensor 36.

| | LEGEND |
|---|---|
| 1. | Pre-filtration with sensor package |
| 2. | Electronics sensor package |
| 3. | Actuator and sensor unit |
| 4. | Pre-filtration components |
| 5. | Electronics post-filtration |
| 6. | Water inlet |
| 7. | Filter water |
| 8. | Shut-off valve |
| 9. | Back-flushable pre-filter with cleaning valve |
| 10. | Safety shut-off valve |
| 11. | Pipe separator |
| 12. | Backflow preventer |
| 13. | Pressure increasing unit |
| 14. | Fine-filter stage 2 |
| 15. | Softening stage |
| 16. | Salt water treatment/brine tank |
| 17. | Weighing unit |
| 18. | Electrolysis cell |
| 19. | Dechlorination stage/carbon filter |
| 20. | Fine-filter stage 3 |
| 21. | Water meter/flow meter |
| 22. | Leakage indicator with sensor |
| 23. | Brine pump |
| 24. | Brine suction valve |
| 25. | Flow throttle |
| 26. | Backflow preventer |
| 27. | Chlorine sensor test valve/calcium check valve I |
| 28. | Chlorine sensor release valve |
| 29. | Chlorine sensor chamber |
| 30. | Chlorine sensor |
| 31. | Chlorine check valve II/fine-filter stage 3 inlet pressure |
| 32. | Chlorine check valve III/fine-filter stage 3 outlet pressure |
| 33. | Chlorine check valve I |
| 34. | Calcium sensor release valve |
| 35. | Calcium sensor chamber |
| 36. | Calcium sensor |
| 37. | Fine filter stage 1 inlet pressure |
| 38. | Fine filter stage 1 outlet pressure |
| 39. | Fine filter stage 2 inlet pressure |
| 40. | Fine filter stage 2 outlet pressure/calcium test valve |
| 41. | Pressure sensor |
| 6a | Lines |
| 6b | |
| 16a | |
| 19a | |
| 24a | |
| 25a | |
| 42. | Platform |
| 43. | Adjustable feet |
| 44. | Electronics |
| 45. | Side boundary |

| | LEGEND |
|---|---|
| 46. | Weighing cell |
| 47. | Measurement foot |
| 48. | Mounting of weighing cell |
| 49. | Shut-off valve |
| 50. | Chlorine-test circulation circuit |
| 51. | Pump |
| 52. | Shut-off valve |
| 53. | Free outlet |

The invention claimed is:

1. A method for monitoring a chlorine sensor of a water treatment system, which includes a dechlorination device in a water line, the method comprising:
supplying electrolytically produced chlorine of a known concentration at regular time intervals to a chlorine sensor, the chlorine sensor in communication with the water line, wherein the chlorine sensor is configured to measure a total chlorine content;
measuring an associated measurement value of the chlorine sensor;
comparing the associated measurement value of the chlorine sensor with the known concentration of electrolytically produced chlorine to provide an indication that the chlorine sensor is accurate; and,
supplying water from an outlet of the dechlorination device to the chlorine sensor device which measures whether the supplied water contains chlorine,
wherein the water treatment system is a reverse osmosis system.

2. The method according to claim 1, wherein the chlorine is produced from a salt solution of a salt water tank.

3. The method according to claim 1, wherein the chlorine is circulated past the chlorine sensor in a line circuit.

4. The method according to claim 1, wherein the chlorine is supplied to the chlorine sensor during the regeneration process of the softener device.

5. A method for monitoring a chlorine sensor of a water treatment system including a dechlorination device in a water line, the method comprising:
supplying chlorine of a known concentration at regular time intervals to the chlorine sensor device, the chlorine sensor device in communication with the water line, wherein the chlorine sensor is configured to measure a total chlorine content;
measuring an associated measurement value of the chlorine sensor;
comparing the associated measurement value of the chlorine sensor with a known concentration of electrolytically produced chlorine to provide an indication that the chlorine sensor is accurate; and,
supplying water from an outlet of the dechlorination device to the chlorine sensor device which measures whether the supplied water contains chlorine,
wherein the water treatment system is a reverse osmosis system.

6. The method according to claim 1, wherein the chlorine is circulated past the chlorine sensor in a line circuit at regular time intervals.

7. The method according to claim 1, wherein the chlorine sensor is an online chlorine sensor.

8. The method according to claim 1, wherein the reverse osmosis system is configured to allow for online access.

9. The method according to claim 8, further comprising:
providing online access to the reverse osmosis system so as to allow for a remote diagnosis about a current operational state of the reverse osmosis system.

10. The method of claim 1, further comprising:
electronically documenting the associated measurement value of the chlorine sensor.

11. The method of claim 1, further comprising:
electronically storing the associated measurement value of the chlorine sensor.

12. The method of claim 11, further comprising:
electronically documenting the associated measurement value of the chlorine sensor.

13. The method according to claim 5, wherein the chlorine sensor is an online chlorine sensor.

14. The method according to claim 5, wherein the reverse osmosis system is configured to allow for online access.

15. The method according to claim 14, further comprising:
providing online access to the reverse osmosis system so as to allow for a remote diagnosis about a current operational state of the reverse osmosis system.

16. The method of claim 5, further comprising:
electronically documenting the associated measurement value of the chlorine sensor.

17. The method of claim 5, further comprising:
electronically storing the associated measurement value of the chlorine sensor.

18. The method of claim 17, further comprising:
electronically documenting the associated measurement value of the chlorine sensor.

* * * * *